(12) United States Patent
Fang et al.

(10) Patent No.: US 10,087,122 B2
(45) Date of Patent: Oct. 2, 2018

(54) SUPPORTED CATALYST, PREPARATION METHOD THEREFOR AND USE THEREOF, AND METHOD FOR PREPARATION OF ISOBUTYLENE FROM HALOMETHANE

(71) Applicants: CHINA PETROLEUM & CHEMICAL CORPORATION, Beijing (CN); Fushun Research Institute of Petroleum and Petrochemicals, SINOPEC CORP., Fushun, Liaoning (CN)

(72) Inventors: Xiangchen Fang, Liaoning (CN); Shudong Zhang, Liaoning (CN); Xinwei Zhang, Liaoning (CN); Xiwen Zhang, Liaoning (CN); Xiaodan Sun, Liaoning (CN); Jie Li, Liaoning (CN); Xiangqian Ni, Liaoning (CN)

(73) Assignees: CHINA PETROLEUM & CHEMICAL CORPORATION, Beijing (CN); FUSHUN RESEARCH INSTITUTE OF PETROLEUM AND PETROCHEMICALS, SINOPEC CORP., Fushun, Liaoning (CN)

( * ) Notice: Subject to any disclaimer, the term of this patent is extended or adjusted under 35 U.S.C. 154(b) by 0 days.

(21) Appl. No.: 15/034,913

(22) PCT Filed: Oct. 28, 2014

(86) PCT No.: PCT/CN2014/089683
§ 371 (c)(1),
(2) Date: May 6, 2016

(87) PCT Pub. No.: WO2015/067133
PCT Pub. Date: May 14, 2015

(65) Prior Publication Data
US 2016/0272555 A1    Sep. 22, 2016

(30) Foreign Application Priority Data

Nov. 7, 2013 (CN) .......................... 2013 1 0546339

(51) Int. Cl.
| | |
|---|---|
| *C07C 1/30* | (2006.01) |
| *B01J 29/40* | (2006.01) |
| *B01J 37/22* | (2006.01) |
| *B01J 27/138* | (2006.01) |
| *C07C 1/26* | (2006.01) |
| *B01J 37/18* | (2006.01) |
| *B01J 23/06* | (2006.01) |
| *B01J 23/10* | (2006.01) |
| *B01J 35/10* | (2006.01) |

(Continued)

(52) U.S. Cl.
CPC .............. *C07C 1/30* (2013.01); *B01J 27/138* (2013.01); *B01J 29/405* (2013.01); *B01J 37/18* (2013.01); *B01J 37/22* (2013.01); *C07C 1/26* (2013.01); *B01J 23/06* (2013.01); *B01J 23/10* (2013.01); *B01J 35/002* (2013.01); *B01J 35/1019* (2013.01); *B01J 35/1042* (2013.01); *B01J 37/0201* (2013.01); *C07C 2521/04* (2013.01); *C07C 2527/138* (2013.01); *C07C 2529/40* (2013.01)

(58) Field of Classification Search
CPC .............. B01J 23/06; B01J 27/00; C07C 1/30
See application file for complete search history.

(56) References Cited

U.S. PATENT DOCUMENTS

| | | | | | |
|---|---|---|---|---|---|
| 2,865,845 | A | * | 12/1958 | Kearby .................... | B01J 27/06 208/136 |
| 4,154,969 | A | * | 5/1979 | Schultz ................... | C07C 37/18 568/729 |

(Continued)

FOREIGN PATENT DOCUMENTS

| | | |
|---|---|---|
| CN | 36107833 A | 7/1988 |
| CN | 1502411 A | 6/2004 |

(Continued)

OTHER PUBLICATIONS

Jieli He et al., "Transformation of Methane to Propylene: A Two-Step Reaction Route Catalyzed by Modified CeO2 Nanocrystals and Zeolites" Angew. Chem. Int. Ed., 51, pp. 2438-2442, doi:10.1002/anie.201104071.

(Continued)

*Primary Examiner* — Douglas B Call
(74) *Attorney, Agent, or Firm* — Novick, Kim & Lee, PLLC; Allen Xue

(57) ABSTRACT

Provided are a supported catalyst, a preparation method therefor and use thereof, and a method for the preparation of isobutylene from halomethane. The catalyst is characterized in that it comprises a carrier and a metallic active component supported on the carrier, wherein the metallic active component comprises zinc oxide and zinc halide. On the basis of the total amount of the catalyst, by weight content, the content of zinc oxide is 0.5%-20%, the content of zinc halide is 10%-50%, and the content of the support is 40%-88%. Compared with the prior art, the catalyst of the present invention can convert halomethane into isobutylene with a high selectivity. With the reaction for preparing of isobutylene by converting bromomethane according to the method of the present invention, the conversion of bromomethane is not less than 90% and the selectivity of isobutylene is not less than 80%.

20 Claims, No Drawings

(51) Int. Cl.
  *B01J 35/00* (2006.01)
  *B01J 37/02* (2006.01)

(56) References Cited

U.S. PATENT DOCUMENTS

| | | | |
|---|---|---|---|
| 5,811,365 A * | 9/1998 | Barry | B01J 23/005 502/329 |
| 6,821,412 B1 * | 11/2004 | Fujukawa | B01J 21/04 208/210 |
| 2004/0127586 A1 * | 7/2004 | Jin | B01J 23/462 518/715 |
| 2004/0138062 A1 * | 7/2004 | Narita | B01J 21/18 502/329 |
| 2010/0004494 A1 | 1/2010 | Li et al. | |
| 2011/0136658 A1 | 6/2011 | Liu et al. | |

FOREIGN PATENT DOCUMENTS

| | | |
|---|---|---|
| CN | 101041609 A | 9/2007 |
| CN | 101284232 A | 10/2008 |
| CN | 101342494 A | 1/2009 |

OTHER PUBLICATIONS

Ivan M. Lorkovic et al., "A novel integrated process for the functionalization of methane and ethane: bromine as mediator", Catalysis Today, vol. 98, Issues 1-2, Nov. 24, 2004, pp. 317-322.

* cited by examiner

SUPPORTED CATALYST, PREPARATION METHOD THEREFOR AND USE THEREOF, AND METHOD FOR PREPARATION OF ISOBUTYLENE FROM HALOMETHANE

FIELD OF THE INVENTION

The present invention relates to a supported catalyst, method for its preparation and use thereof, and a method for preparation of isobutylene from halomethane by using this supported catalyst.

BACKGROUND OF THE INVENTION

Isobutylene is an important basic organic chemical raw material. It has numerous derivatives. Its upstream and downstream industrial chains are complex. Its consumption structure is in diversified trends. From isobutylene, many products with high added value may be prepared, such as: butyl rubber, polyisobutylene, methyl tertiary-butyl ether, isoprene, polymethyl methacrylate and many other organic chemical raw materials and fine chemical products. As the market size of isobutylene downstream products keeps expanding, the imbalance between supply and demand will get more prominent. Particularly, under the background of increasing depletion of petroleum resources, the output of isobutylene has become a critical bottleneck holding back the development of downstream industry. Therefore, it is urgent to develop an isobutylene preparation route rather than a petroleum route.

Methane is a main component of natural gas, so methane conversion and utilization becomes an important research content of natural gas chemical technology. Particularly, in the recent years, under the general background of shale gas development and utilization, if isobutylene can be made from methane, it will be a new way to obtain isobutylene. However, methane has stable properties and is not easily activated, so it turns to be a bottleneck of chemical utilization of methane. Many domestic and foreign researchers have carried out the research of methane activation and conversion. The technology of halogen functionalization and then conversion of methane hopefully will become an important breakthrough to the technical problem of methane conversion.

From halomethane, many chemical products may be prepared. CN101041609A and CN101284232A disclose a method of converting methane into bromomethane under the action of oxygen and $HBr/H_2O$ and then taking further reaction of bromomethane to generate $C_3-C_{13}$ mixed high-carbon hydrocarbons. The selectivity of hydrocarbons of $C_5$ or higher is 70%. HBr is used to bromize methane in the first reactor and released in the second reactor. After recovery, it is used in the first reaction again to realize cyclic use of HBr. Wang Ye et al (Jieli He, Ting Xu, Zhihui Wang, et. al. Angew. Chem. Int. Ed. 2012, 51, 2438-2442) discloses a modified molecular sieve catalyst of propylene from halomethane and preparation method thereof. By using a molecular sieve modified and treated with fluorinated compound to obtain an acidic catalyst containing an appropriate micropore structure, this catalyst may effectively catalyze halomethane and convert it into propylene. In the preparation and conversion of propylene from bromomethane, the single-pass bromomethane conversion rate of the prepared catalyst is 35-99% and the selectivity of propylene is 27-70%; in the preparation and conversion of propylene from chloromethane, the single-pass chloromethane conversion rate is 30-99% and the selectivity of propylene is 15-70%. Ivan M. Lorkovic et al (Ivan M. Lorkovic, Aysen Yilmaz, Gurkan A. Yilmaz, et al. Catalysis Today, 2004, 98, 317-322) also put forth a bromine circulation of using bromine to react with hydrocarbons in natural gas to generate bromo-hydrocarbons, then converting bromo-hydrocarbons into dimethyl ether, methanol and metal bromide on a metal oxide catalyst, and regenerating metal bromide by oxygen to obtain metal oxide and release simple substance bromine. At present, the target products of halomethane conversion in the existing literature are methanol, dimethyl ether, acetic acid, high-carbon hydrocarbon, ethylene and propylene. In the technologies in which low-carbon olefins with high added value are target products, the selectivity of a single product is not high. So far there is no report on highly selective synthesis of isobutylene from bromomethane.

SUMMARY OF THE INVENTION

To address the shortcomings of prior art, the present invention provides a supported catalyst for highly selective generation of isobutylene from halomethane and its preparation method and use. According to one aspect of the present invention, the present invention provides a supported catalyst, wherein the catalyst contains a support and a metallic active component supported on the support; the metallic active component contains zinc oxide and zinc halide, and the content of zinc oxide is 0.5 wt. %-20 wt. %, the content of zinc halide is 10 wt. %-50 wt. %, and the content of the support is 40 wt. %-88 wt. % based on the total weight of the catalyst.

According to the second aspect of the present invention, the present invention provides a method for preparing a supported catalyst, wherein the method includes the following steps: introducing zinc oxide to a support and then halogenating the resulted support after introducing zinc oxide.

According to the third aspect of the present invention, the present invention provides a use of the supported catalyst of the present invention in preparation of isobutylene.

According to the fourth aspect of the present invention, the present invention provides a method for preparation of isobutylene from halomethane, wherein the method includes carrying out hydrogen reduction activation of the supported catalyst of the present invention to make the content of halogen in the activated catalyst be 20 wt. %-90 wt. % of the total content of halogen in the supported catalyst without reduction, then contacting halomethane with the activated catalyst to prepare isobutylene. Compared with prior art, the catalyst of the present invention may convert halomethane into isobutylene with high selectivity. The reaction for conversion and preparation of isobutylene from bromomethane is conducted by the method of the present invention. The bromomethane conversion rate is 90% or more and the selectivity of isobutylene is 80% or more. The preparation method of this catalyst is simple and can be easily industrialized. The method for preparation and conversion of isobutylene from bromomethane in the present invention has such advantages as moderate reaction conditions and high product selectivity, can be easily industrialized and has a broad application prospect.

DETAILED DESCRIPTION OF THE EMBODIMENTS

According to one aspect of the present invention, the present invention provides a supported catalyst, wherein the catalyst contains a support and a metallic active component supported on the support, the metallic active component contains zinc oxide and zinc halide, and the content of zinc oxide is 0.5 wt. %-20 wt. %, the content of zinc halide is 10 wt. %-50 wt. %, and the content of the support is 40 wt. %-88 wt. % based on the total weight of the catalyst.

Preferably, based on the total weight of the catalyst, the content of zinc oxide is 1 wt. %-15 wt. %, the content of zinc halide is 15 wt. %-45 wt. %, and the content of the support is 50 wt. %-84 wt. %, more preferably, the content of zinc oxide is 1 wt. %-9 wt. %, the content of zinc halide is 18 wt. %-39 wt. %, and the content of the support is 55 wt. %-80 wt. % based on the total weight of the catalyst.

According to the present invention, the zinc halide may be selected from one or more of zinc fluoride, zinc chloride, zinc bromide and zinc iodide. The support may be one or more of aluminum oxide, silicon oxide and ZSM-5 molecular sieve.

Preferably, the zinc halide is zinc bromide, and the support is aluminum oxide. The aluminum oxide may be γ-aluminum oxide and/or θ-aluminum oxide.

According to the supported catalyst of the present invention, preferably, this catalyst further contains an appropriate amount of promoter, which is selected from one or more of Ti, Zr, Ce and La. More preferably, the promoter is Zr.

The weight content of the promoter calculated on element is 0.1 wt. %-10 wt. %, more preferably 0.5 wt. %-5 wt. %, still more preferably 0.5 wt. %-3 wt. % based on the total weight of the catalyst.

According to the supported catalyst of the present invention, it is determined by $NH_3$-TPD method that the total acidity of 450° C. or less in the catalyst is 0.5 mmol/g-1.3 mmol/g, and the acidity of 250° C.-350° C. is 20%-90% of the total acidity of 450° C. or less; preferably, the total acidity of 450° C. or less in the catalyst is 0.6 mmol/g-1.2 mmol/g, and the acidity of 250° C.-350° C. is 30%-80% of the total acidity of 450° C. or less; more preferably, the total acidity of 450° C. or less in the catalyst is 0.7 mmol-1.1 mmol/g, and the acidity of 250° C.-350° C. is 40%-80% of the total acidity of 450° C. or less. In the present invention, the acids determined by $NH_3$-TPD method in correspondence to 150° C.-250° C. are weak acids, the acids in correspondence to 250° C.-400° C. are moderate strong acids, and the acids in correspondence to 400° C.-500° C. are strong acids; the sum of the acid content of weak acids, moderately strong acids and strong acids are total acid content.

According to the method for preparing a supported catalyst in the present invention, wherein the method includes the following steps: introducing zinc oxide to the support and then halogenating the resulted support after introducing zinc oxide.

The amount of introduced zinc oxide and the conditions of halogenation make the content of zinc oxide be 0.5 wt. %-20 wt. %, the content of zinc halide be 10 wt. %-50 wt. %, and the content of the support be 40 wt. %-88 wt. % based on the total weight of the obtained supported catalyst. Preferably, the content of zinc oxide is 1 wt. %-15 wt. %, the content of zinc halide is 15 wt. %-40 wt. %, and the content of the support is 50 wt. %-84 wt. %, more preferably, the content of zinc oxide is 1 wt. %-9 wt. %, the content of zinc halide is 18 wt. %-39 wt. %, and the content of the support is 55 wt. %-80 wt. %.

According to the present invention, various means may be adopted to halogenate the support containing the introduced zinc oxide as long as an appropriate amount of zinc oxide in it is converted into zinc halide. Preferably, the mean of the halogenation includes contacting gaseous-phase halogen-containing compound with the support containing the introduced zinc oxide under the contact conditions that make the zinc oxide on the support partially converted into zinc halide.

Gaseous-phase halogen-containing compound may directly contact the support containing the introduced zinc oxide. Alternatively, gaseous-phase halogen-containing compound may contact the support containing the introduced zinc oxide in a form of a mixed gas of gaseous-phase halogen-containing compound and inert gas. In the mixed gas, the concentration of the gaseous-phase halogen-containing compound is not less than 20 v/v %., preferably not less than 30 v/v %, more preferably 30-90 v/v %, still more preferably 50-80 v/v %.

The gaseous-phase halogen-containing compound may be various kinds of halogen-containing compounds that are gaseous under the contact conditions, preferably halomethane, more preferably one or more of monohalomethane, bihalomethane and trihalomethane, still more preferably monohalomethane.

The halogen may be one or more of F, Cl, Br and I, preferably Cl and/or Br.

More preferably, the gaseous-phase halogen-containing compound is monobromomethane.

According to the present invention, the preferred mean of the contact includes putting the support containing the introduced zinc oxide in a continuous flow fixed bed reactor, raising temperature to 150° C.-400° C. in an inert atmosphere, and inputting gaseous-phase halogen-containing compound or a mixed gas containing gaseous-phase halogen-containing compound. The space velocity is 50 $h^{-1}$-1000 $h^{-1}$, the contact pressure is 0.1 MPa-0.5 MPa and the time is 0.5 h-8 h. Preferably, temperature is raised to 180° C.-350° C. in an inert atmosphere, more preferably, the temperature is raised to 200° C.-300° C., the space velocity is 100 $h^{-1}$-500 $h^{-1}$, the contact pressure is 0.1 MPa-0.3 MPa and the time is 1 h-4 h. The pressure is absolute pressure. The space velocity is space velocity by volume.

According to the present invention, zinc oxide may be introduced to the support in various existing means. For example, it may be introduced by impregnation, or by kneading during forming, or by gelling and co-precipitation during preparation of the support. Impregnation is preferred, i.e.: making a dissolvable compound of zinc into an impregnation liquid, then impregnating the support in the impregnation liquid and then drying and calcinating them. The dissolvable compound of zinc may be dissolvable inorganic salt and/or organic salt of zinc, such as: one or more of chloride, nitrate, sulfate, hydrochloride, acetate and citrate. As to element zinc, the concentration of the impregnation liquid is 5 g/L-300 g/L, preferably 20 g/L-200 g/L, more preferably 40 g/L-160 g/L. Impregnation in an equal volume or oversaturated impregnation may be adopted.

When the catalyst of the present invention further contains a promoter, the promoter may be introduced before, after or simultaneously with zinc oxide. It may be introduced by impregnation, or by kneading during forming, or by gelling and co-precipitation during preparation of the support. Impregnation is preferred, specifically: adopting a zinc salt and promoter metal salt solution to impregnate the formed support, drying and calcinating and then carrying out halogenation, or adopting a zinc salt solution to impregnate the formed support at first, drying and calcinating and then carrying out halogenation, lastly impregnating in a promoter metal salt solution and then drying and calcinating to obtain halomethane, which is used to make isobutylene catalyst.

The drying temperature may be 50° C.-200° C., preferably 60° C.-150° C., more preferably 80° C.-120° C.; the drying time is 1 h-24 h, preferably 4 h-8 h; the drying may be vacuum drying, or drying under protection of inert gas, or drying in an air atmosphere; the calcination temperature is 200° C.-800° C., preferably 400° C.-600° C.; the calcination time is 1 h-24 h, preferably 4 h-8 h; the calcination may be under protection of inert gas, or in an air atmosphere.

The support may be an existing commercial product, or prepared by a method well known to those skilled in the art. The support may be prepared according to need or made into an appropriate granular shape, such as: bar, slice, cylinder or sphere. The forming may be based on general knowledge of the art.

The present invention also provides application of the supported catalyst of the present invention in the preparation of isobutylene.

The present invention further provides a method for preparation of isobutylene from halomethane, including carrying out hydrogen reduction activation of the supported catalyst of the present invention to make the content of halogen in the activated catalyst be 20 wt. %-90 wt. % of the total content of halogen in the supported catalyst without reduction, then contacting halomethane with the activated catalyst to prepare isobutylene.

According to the present invention, the conditions of the hydrogen reduction activation make the content of halogen in the activated catalyst be preferably 30 wt. %-80 wt. % of the total content of halogen in the supported catalyst without reduction, more preferably 40 wt. %-80 wt. %.

According to an embodiment of the present invention, the way of hydrogen reduction activation includes raising temperature of the catalyst to 300° C.-600° C. in an inert atmosphere; then inputting hydrogen or a mixed gas of hydrogen and inert gas at a space velocity of 200 $h^{-1}$-2000 $h^{-1}$ and holding pressure at 0.1 MPa-0.5 MPa for 2 h-16 h. The volume percentage of hydrogen in the mixed gas is 10%-95%. Preferably, raising temperature to 350° C.-550° C.; then inputting hydrogen or a mixed gas of hydrogen and inert gas at a space velocity of 500 $h^{-1}$-1000 $h^{-1}$ and holding pressure at 0.1 MPa-0.3 MPa for 4 h-8 h. The volume percentage of hydrogen in the mixed gas is 30%-90%.

According to the present invention, the halomethane may be one or more of monohalomethane, bihalomethane and trihalomethane, preferably, one or more of monobromomethane, bibromomethane and tribromomethane.

Preferably, the contact conditions include reaction temperature 150° C.-350° C., reaction pressure 0.1 MPa-5 MPa and space velocity 50 $h^{-1}$-1000 $h^{-1}$; more preferably, reaction temperature 180° C.-300° C., still more preferably 200-270° C.; reaction pressure 0.1 MPa-3 MPa; space velocity 200 $h^{-1}$-500 $h^{-1}$. According to an embodiment of the present invention, the method for preparing isobutylene from halomethane includes raising temperature of the catalyst to 300° C.-600° C. in an inert atmosphere, preferably 350° C.-550° C.; then inputting hydrogen or a mixed gas of hydrogen and inert gas at a space velocity of 200 $h^{-1}$-2000 $h^{-1}$, preferably 500 $h^{-1}$-1000 $h^{-1}$; and after treating at 0.1 MPa-0.5 MPa (absolute pressure), preferably 0.1 MPa-0.3 MPa (absolute pressure) for 2 h-16 h, preferably 4 h-8 h, lowering temperature to reaction temperature and inputting halomethane to take reaction. The volume percentage of hydrogen in the mixed gas is 10%-95%, preferably 30%-90%, more preferably 50%-90%.

In the use of the present invention, the raw material may alternatively be a mixed gas of halomethane and inert gas, of which the volume concentration of halomethane is 10%-90%, preferably 30%-80%. The inert gas involved in the use of the present invention is nitrogen, argon, helium and other gases that don't take reaction under the conditions involved in the present invention, preferably nitrogen. According to the use of the present invention, the reaction for preparing isobutylene from halomethane may be conducted in any form of existing reactors, such as: reactors in form of fixed bed, fluidized bed, fixed fluidized bed, moving bed, slurry bed or bubbling bed, preferably fixed bed and fluidized bed reactors.

Thereafter, the present invention is further described by referring to examples, but they are not intended to limit the present invention.

In the following examples and comparative examples, acid content is determined by $NH_3$-TPD method. The adopted instrument is AutoChem 2920 chemical adsorption instrument of American MICROMERITICS. The concrete determination process is as follows: purging the sample with helium at 450° C. for 1 h, reducing temperature to 150° C., introducing a mixed gas of ammonia and helium, with ammonia volume content of 10%, and carrying out pulse adsorption for five times to achieve a balance; purging with helium for 2 h, and then raising temperature according to a temperature increase speed program of 10° C./min and conducting desorption of ammonia till 450° C.; detecting ammonia by TCD detector after desorption and quantitatively calculating the acidity on catalyst surface.

In the following examples and comparative examples, the content of element Br and that of element Zn are determined by XRF (X-ray fluorescent spectroscopy) method. The adopted instrument is ZSX X-ray fluorescence spectrophotometer of Japanese Rigaku. The content of $ZnBr_2$ is calculated based on the content of element Br. The content of ZnO is calculated based on total Zn content minus the content of Zn in $ZnBr_2$.

Example 1

Weigh an appropriate amount of zinc nitrate, dissolve it in deionized water, support it to aluminum oxide (pore volume 0.71 ml/g, specific surface area 236 m²/g, bar type, equivalent diameter 1.5 mm) support by the method of incipient wetness impregnation, dry at 80° C. for 8 h and calcinate at 600° C. for 4 h to obtain catalyst precursor $ZnO/Al_2O_3$. Put 5 g of the catalyst precursor in a continuous flow fixed bed reactor and treat the catalyst precursor with monobromomethane under the conditions of 250° C., 0.2 MPa (absolute pressure), 100 $h^{-1}$ and 2 h to obtain a catalyst for preparation of isobutylene from halomethane, marked as C-1. The weight composition of the catalyst is that the weight content of $ZnBr_2$ is 27%, the weight content of ZnO is 6%, the total acidity of 450° C. or less in the catalyst is 0.92 mmol/g, and the acidity of 250° C.-350° C. is 55.1% of the total acidity of 450° C. or less.

The reaction for preparation of isobutylene from bromomethane takes place in a continuous fluidized fixed bed micro-reactor. The loading amount of catalyst is 5 g. The feed gas is a mixed gas of monobromomethane and nitrogen of which volume concentration of monobromomethane is 50%. The reaction temperature is 230° C., reaction pressure is 1 MPa (absolute pressure) and space velocity is 500 $h^{-1}$. Before input of feed gas, the catalyst is activated in a hydrogen atmosphere. The conditions of reduction are 400° C., 0.2 MPa (absolute pressure) and 1000 $h^{-1}$. The time of reduction is 4 h. The content of halogen in the catalyst after reduction is 67.51% of the total content of halogen in the catalyst before reduction. After the reaction has become stable for one hour, samples are taken and analyzed. The reaction result is shown in Table 1.

Example 2

Weigh an appropriate amount of zinc nitrate, dissolve it in deionized water, support it to aluminum oxide (pore volume 0.71 ml/g, specific surface area 236 $m^2/g$, bar type, equivalent diameter 1.5 mm) support by the method of incipient wetness impregnation, dry at 120° C. for 4 h and calcinate at 500° C. for 8 h to obtain catalyst precursor $ZnO/Al_2O_3$. Put 5 g of the catalyst precursor in a continuous flow fixed bed reactor and treat the catalyst precursor with a mixed gas of monobromomethane and nitrogen of which volume concentration of monobromomethane is 80% under the conditions of 250° C., 0.3 MPa (absolute pressure), 300 $h^{-1}$ and 2 h to obtain a catalyst for preparation of isobutylene from halomethane, marked as C-2. The weight composition of the obtained catalyst is that the weight content of $ZnBr_2$ as to bromide is 30%, the weight content of ZnO is 4%, the total acidity of 450° C. or less in the catalyst is 0.93 mmol/g, and the acidity of 250° C.-350° C. is 63.2% of the total acidity of 450° C. or less.

The reaction for preparation of isobutylene from bromomethane takes place in a continuous fluidized fixed bed micro-reactor. The loading amount of catalyst is 5 g. The feed gas is a mixed gas of monobromomethane and nitrogen of which volume concentration of monobromomethane is 70%. The reaction temperature is 230° C., reaction pressure is 2 MPa (absolute pressure) and space velocity is 200 $h^{-1}$. Before input of feed gas, the catalyst is activated in a mixed atmosphere containing hydrogen. The volume content of hydrogen in the mixed gas is 80%. The conditions of reduction are 450° C., 0.3 MPa (absolute pressure) and 800 $h^{-1}$. The time of reduction is 4 h. The content of halogen in the catalyst after reduction is 53.47% of the total content of halogen in the catalyst before reduction. After the reaction has become stable for one hour, samples are taken and analyzed. The reaction result is shown in Table 1.

Example 3

Weigh an appropriate amount of zinc nitrate, dissolve it in deionized water, support it to aluminum oxide (pore volume 0.71 ml/g, specific surface area 236 $m^2/g$, bar type, equivalent diameter 1.5 mm) support by the method of incipient wetness impregnation, dry under vacuum at 100° C. for 8 h and calcinate at 400° C. for 8 h to obtain catalyst precursor $ZnO/Al_2O_3$. Put 5 g of the catalyst precursor in a continuous flow fixed bed reactor and treat the catalyst precursor with a mixed gas of monobromomethane and nitrogen of which volume concentration of monobromomethane is 30% under the conditions of 300° C., 0.1 MPa (absolute pressure), 500 $h^{-1}$ and 4 h to obtain a catalyst for preparation of isobutylene from halomethane, marked as C-3. The weight composition of the obtained catalyst is that the weight content of $ZnBr_2$ as to bromide is 33%, the weight content of ZnO as to oxide is 2%, the total acidity of 450° C. or less in the catalyst is 0.95 mmol/g, and the acidity of 250° C.-350° C. is 75.5% of the total acidity of 450° C. or less.

The reaction for preparation of isobutylene from bromomethane takes place in a continuous fluidized fixed bed micro-reactor. The loading amount of catalyst is 5 g. The feed gas is a mixed gas of monobromomethane and nitrogen of which volume concentration of monobromomethane is 80%. The reaction temperature is 200° C., reaction pressure is 3 MPa (absolute pressure) and space velocity is 350 $h^{-1}$. Before input of feed gas, the catalyst is activated in a mixed atmosphere containing hydrogen. The volume content of hydrogen in the mixed gas is 50%. The conditions of reduction are 500° C., 0.1 MPa (absolute pressure) and 500 $h^{-1}$. The time of reduction is 4 h. The content of halogen in the catalyst after reduction is 47.22% of the total content of halogen in the catalyst before reduction. After the reaction has become stable for one hour, samples are taken and analyzed. The reaction result is shown in Table 1.

Example 4

Weigh an appropriate amount of zinc nitrate, dissolve it in deionized water, support it to aluminum oxide (pore volume 0.71 ml/g, specific surface area 236 $m^2/g$, bar type, equivalent diameter 1.5 mm) support by the method of incipient wetness impregnation, dry at 120° C. for 4 h and calcinate at 500° C. for 8 h to obtain catalyst precursor $ZnO/Al_2O_3$. Put 5 g of the catalyst precursor in a continuous flow fixed bed reactor and treat the catalyst precursor with monobromomethane under the conditions of 200° C., 0.3 MPa (absolute pressure), 300 $h^{-1}$ and 1 h to obtain a catalyst for preparation of isobutylene from halomethane, marked as C-4. The weight composition of the obtained catalyst is that the weight content of $ZnBr_2$ as to bromide is 18%, the weight content of ZnO as to oxide is 2%, the total acidity of 450° C. or less in the catalyst is 0.72 mmol/g, and the acidity of 250° C.-350° C. is 66.8% of the total acidity of 450° C. or less.

The reaction for preparation of isobutylene from bromomethane takes place in a continuous fluidized fixed bed micro-reactor. The loading amount of catalyst is 5 g. The feed gas is a mixed gas of monobromomethane and nitrogen of which volume concentration of monobromomethane is 30%. The reaction temperature is 270° C., reaction pressure is 2 MPa (absolute pressure) and space velocity is 350 $h^{-1}$. Before input of feed gas, the catalyst is activated in a mixed atmosphere containing hydrogen. The volume content of hydrogen in the mixed gas is 70%. The conditions of reduction are 350° C., 0.3 MPa (absolute pressure) and 800 $h^{-1}$. The time of reduction is 6 h. The content of halogen in the catalyst after reduction is 57.81% of the total content of halogen in the catalyst before reduction. After the reaction has become stable for one hour, samples are taken and analyzed. The reaction result is shown in Table 1.

Example 5

Weigh an appropriate amount of zinc nitrate, dissolve it in deionized water, support it to aluminum oxide (pore volume 0.71 ml/g, specific surface area 236 $m^2/g$, bar type, equivalent diameter 1.5 mm) support by the method of incipient wetness impregnation, dry at 100° C. for 6 h and calcinate at 500° C. for 6 h under protection of nitrogen to obtain catalyst precursor $ZnO/Al_2O_3$. Put 5 g of the catalyst precursor in a continuous flow fixed bed reactor and treat the catalyst precursor with a mixed gas of monobromomethane and nitrogen of which volume concentration of monobromomethane is 70% under the conditions of 200° C., 0.3 MPa (absolute pressure), 300 $h^{-1}$ and 2 h to obtain a catalyst for preparation of isobutylene from halomethane, marked as C-5. The weight composition of the obtained catalyst is that the weight content of $ZnBr_2$ as to bromide is 39%, the weight content of ZnO as to oxide is 6%, the total acidity of 450° C. or less in the catalyst is 0.98 mmol/g, and the acidity of 250° C.-350° C. is 64.1% of the total acidity of 450° C. or less.

The reaction for preparation of isobutylene from bromomethane takes place in a continuous fluidized fixed bed micro-reactor. The loading amount of catalyst is 5 g. The feed gas is monobromomethane. The reaction temperature is 270° C., reaction pressure is 2 MPa (absolute pressure) and space velocity is 350 $h^{-1}$. Before input of feed gas, the catalyst is activated in a mixed atmosphere containing hydrogen. The volume content of hydrogen in the mixed gas is 60%. The conditions of reduction are 550° C., 0.3 MPa (absolute pressure) and 800 $h^{-1}$. The time of reduction is 8 h. The content of halogen in the catalyst after reduction is 41.37% of the total content of halogen in the catalyst before reduction. After the reaction has become stable for one hour, samples are taken and analyzed. The reaction result is shown in Table 1.

Example 6

Weigh an appropriate amount of zinc nitrate, dissolve it in deionized water, support it to aluminum oxide (pore volume 0.71 ml/g, specific surface area 236 $m^2$/g, bar type, equivalent diameter 1.5 mm) support by the method of incipient wetness impregnation, dry at 120° C. in a nitrogen atmosphere for 4 h and calcinate at 500° C. in a nitrogen atmosphere for 4 h to obtain catalyst precursor $ZnO/Al_2O_3$. Put 5 g of the catalyst precursor in a continuous flow fixed bed reactor and treat the catalyst precursor with monobromomethane under the conditions of 250° C., 0.2 MPa (absolute pressure), 100 $h^{-1}$ and 1 h to obtain a catalyst for preparation of isobutylene from halomethane, marked as C-6. The weight composition of the obtained catalyst is that the weight content of $ZnBr_2$ as to bromide is 35%, the weight content of ZnO as to oxide is 9%, the total acidity of 450° C. or less in the catalyst is 0.94 mmol/g, and the acidity of 250° C.-350° C. is 57.3% of the total acidity of 450° C. or less.

The reaction for preparation of isobutylene from bromomethane takes place in a continuous fluidized fixed bed micro-reactor. The loading amount of catalyst is 5 g. The feed gas is a mixed gas of monobromomethane and nitrogen of which volume concentration of monobromomethane is 50%. The reaction temperature is 230° C., reaction pressure is 0.1 MPa (absolute pressure) and space velocity is 500 $h^{-1}$. Before input of feed gas, the catalyst is activated in a mixed atmosphere containing hydrogen. The volume content of hydrogen in the mixed gas is 80%. The conditions of reduction are 450° C., 0.2 MPa (absolute pressure) and 1000 $h^{-1}$. The time of reduction is 4 h. The content of halogen in the catalyst after reduction is 58.39% of the total content of halogen in the catalyst before reduction. After the reaction has become stable for one hour, samples are taken and analyzed. The reaction result is shown in Table 1.

Example 7

Weigh an appropriate amount of zinc nitrate, dissolve it in deionized water, support it to aluminum oxide (pore volume 0.71 ml/g, specific surface area 236 $m^2$/g, bar type, equivalent diameter 1.5 mm) support by the method of incipient wetness impregnation, dry at 120° C. for 4 h and calcinate at 500° C. for 4 h to obtain catalyst precursor $ZnO/Al_2O_3$. Put 5 g of the catalyst precursor in a continuous flow fixed bed reactor and treat the catalyst precursor with mixed gas of monobromomethane and nitrogen of which volume concentration of monobromomethane is 90% under the conditions of 300° C., 0.1 MPa (absolute pressure), 500 $h^{-1}$ and 4 h to obtain a catalyst for preparation of isobutylene from halomethane, marked as C-7. The weight composition of the obtained catalyst is that the weight content of $ZnBr_2$ as to bromide is 20%, the weight content of ZnO as to oxide is 1%, the total acidity of 450° C. or less in the catalyst is 0.79 mmol/g, and the acidity of 250° C.-350° C. is 74.9% of the total acidity of 450° C. or less.

The reaction for preparation of isobutylene from bromomethane takes place in a continuous fluidized fixed bed micro-reactor. The loading amount of catalyst is 5 g. The feed gas is a mixed gas of monobromomethane and nitrogen of which volume concentration of monobromomethane is 80%. The reaction temperature is 200° C., reaction pressure is 3 MPa (absolute pressure) and space velocity is 350 $h^{-1}$. Before input of feed gas, the catalyst is activated in a mixed atmosphere containing hydrogen. The volume content of hydrogen in the mixed gas is 90%. The conditions of reduction are 500° C., 0.1 MPa (absolute pressure) and 500 $h^{-1}$. The time of reduction is 6 h. The content of halogen in the catalyst after reduction is 51.94% of the total content of halogen in the catalyst before reduction. After the reaction has become stable for one hour, samples are taken and analyzed. The reaction result is shown in Table 1.

Example 8

Weigh an appropriate amount of zinc nitrate and zirconium nitrate, dissolve it in deionized water, support it to aluminum oxide (pore volume 0.71 ml/g, specific surface area 236 $m^2$/g, bar type, equivalent diameter 1.5 mm) support by the method of incipient wetness impregnation, dry at 120° C. for 4 h and calcinate at 500° C. for 4 h to obtain catalyst precursor $ZnO$—$Zr/Al_2O_3$. Put 5 g of the catalyst precursor in a continuous flow fixed bed reactor and treat the catalyst precursor with a mixed gas of monobromomethane and nitrogen of which volume concentration of monobromomethane is 80% under the conditions of 250° C., 0.3 MPa (absolute pressure), 300 $h^{-1}$ and 2 h to obtain a catalyst for preparation of isobutylene from halomethane, marked as C-8. The weight composition of the obtained catalyst is that the weight content of $ZnBr_2$ as to bromide is 30%, the weight content of ZnO as to oxide is 4%, the weight content of Zr as to element is 2%, the total acidity of 450° C. or less in the catalyst is 0.97 mmol/g, and the acidity of 250° C.-350° C. is 69.7% of the total acidity of 450° C. or less.

The reaction for preparation of isobutylene from bromomethane takes place in a continuous fluidized fixed bed micro-reactor. The loading amount of catalyst is 5 g. The feed gas is a mixed gas of monobromomethane and nitrogen of which volume concentration of monobromomethane is 70%. The reaction temperature is 230° C., reaction pressure is 2 MPa (absolute pressure) and space velocity is 200 $h^{-1}$. Before input of feed gas, the catalyst is activated in a mixed atmosphere containing hydrogen. The volume content of hydrogen in the mixed gas is 80%. The conditions of reduction are 450° C., 0.3 MPa (absolute pressure) and 800 $h^{-1}$. The time of reduction is 4 h. The content of halogen in the catalyst after reduction is 39.14% of the total content of halogen in the catalyst before reduction. After the reaction has become stable for one hour, samples are taken and analyzed. The reaction result is shown in Table 1.

Example 9

Weigh an appropriate amount of zinc nitrate and cerium nitrate, dissolve it in deionized water, support it to aluminum oxide (pore volume 0.71 ml/g, specific surface area 236 m²/g, bar type, equivalent diameter 1.5 mm) support by the method of incipient wetness impregnation, dry at 120° C. for 4 h and calcinate at 500° C. for 4 h to obtain catalyst precursor ZnO—Ce/Al$_2$O$_3$. Put 5 g of the catalyst precursor in a continuous flow fixed bed reactor and treat the catalyst precursor with a mixed gas of monobromomethane and nitrogen of which volume concentration of monobromomethane is 80% under the conditions of 250° C., 0.3 MPa (absolute pressure), 300 h$^{-1}$ and 2 h to obtain a catalyst for preparation of isobutylene from halomethane, marked as C-9. The weight composition of the obtained catalyst is that the weight content of ZnBr$_2$ as to bromide is 30%, the weight content of ZnO as to oxide is 4%, the weight content of Ce as to element is 1%, the total acidity of 450° C. or less in the catalyst is 0.91 mmol/g, and the acidity of 250° C.-350° C. is 68.9% of the total acidity of 450° C. or less.

The reaction for preparation of isobutylene from bromomethane takes place in a continuous fluidized fixed bed micro-reactor. The loading amount of catalyst is 5 g. The feed gas is a mixed gas of monobromomethane and nitrogen of which volume concentration of monobromomethane is 70%. The reaction temperature is 230° C., reaction pressure is 2 MPa (absolute pressure) and space velocity is 200 h$^{-1}$. Before input of feed gas, the catalyst is activated in a mixed atmosphere containing hydrogen. The volume content of hydrogen in the mixed gas is 80%. The conditions of reduction are 450° C., 0.3 MPa (absolute pressure) and 800 h$^{-1}$. The time of reduction is 4 h. The content of halogen in the catalyst after reduction is 63.73% of the total content of halogen in the catalyst before reduction. After the reaction has become stable for one hour, samples are taken and analyzed. The reaction result is shown in Table 1.

Example 10

Weigh an appropriate amount of zinc nitrate and lanthanum nitrate, dissolve it in deionized water, support it to aluminum oxide (pore volume 0.71 ml/g, specific surface area 236 m²/g, bar type, equivalent diameter 1.5 mm) support by the method of incipient wetness impregnation, dry at 120° C. for 4 h and calcinate at 500° C. for 4 h to obtain catalyst precursor ZnO—La/Al$_2$O$_3$. Put 5 g of the catalyst precursor in a continuous flow fixed bed reactor and treat the catalyst precursor with a mixed gas of monobromomethane and nitrogen of which volume concentration of monobromomethane is 80% under the conditions of 250° C., 0.3 MPa (absolute pressure), 300 h$^{-1}$ and 2 h to obtain a catalyst for preparation of isobutylene from halomethane, marked as C-10. The weight composition of the obtained catalyst is that the weight content of ZnBr$_2$ as to bromide is 30%, the weight content of ZnO as to oxide is 4%, the weight content of La as to element is 0.5%, the total acidity of 450° C. or less in the catalyst is 0.87 mmol/g, and the acidity of 250° C.-350° C. is 65.3% of the total acidity of 450° C. or less.

The reaction for preparation of isobutylene from bromomethane takes place in a continuous fluidized fixed bed micro-reactor. The loading amount of catalyst is 5 g. The feed gas is a mixed gas of monobromomethane and nitrogen of which volume concentration of monobromomethane is 70%. The reaction temperature is 230° C., reaction pressure is 2 MPa (absolute pressure) and space velocity is 200 h$^{-1}$. Before input of feed gas, the catalyst is activated in a mixed atmosphere containing hydrogen. The volume content of hydrogen in the mixed gas is 80%. The conditions of reduction are 450° C., 0.3 MPa (absolute pressure) and 800 h$^{-1}$. The time of reduction is 4 h. The content of halogen in the catalyst after reduction is 62.72% of the total content of halogen in the catalyst before reduction. After the reaction has become stable for one hour, samples are taken and analyzed. The reaction result is shown in Table 1.

Example 11

Weigh an appropriate amount of zinc nitrate and titanium nitrate, dissolve it in deionized water, support it to aluminum oxide (pore volume 0.71 ml/g, specific surface area 236 m²/g, bar type, equivalent diameter 1.5 mm) support by the method of incipient wetness impregnation, dry at 120° C. for 4 h and calcinate at 500° C. for 4 h to obtain catalyst precursor ZnO—Ti/Al$_2$O$_3$. Put 5 g of the catalyst precursor in a continuous flow fixed bed reactor and treat the catalyst precursor with a mixed gas of monobromomethane and nitrogen of which volume concentration of monobromomethane is 80% under the conditions of 250° C., 0.3 MPa (absolute pressure), 300 h$^{-1}$ and 2 h to obtain a catalyst for preparation of isobutylene from halomethane, marked as C-11. The weight composition of the obtained catalyst is that the weight content of ZnBr$_2$ as to bromide is 30%, the weight content of ZnO as to oxide is 4%, the weight content of Ti as to element is 3%, the total acidity of 450° C. or less in the catalyst is 0.96 mmol/g, and the acidity of 250° C.-350° C. is 63.4% of the total acidity of 450° C. or less.

The reaction for preparation of isobutylene from bromomethane takes place in a continuous fluidized fixed bed micro-reactor. The loading amount of catalyst is 5 g. The feed gas is a mixed gas of monobromomethane and nitrogen of which volume concentration of monobromomethane is 70%. The reaction temperature is 230° C., reaction pressure is 2 MPa (absolute pressure) and space velocity is 200 h$^{-1}$. Before input of feed gas, the catalyst is activated in a mixed atmosphere containing hydrogen. The volume content of hydrogen in the mixed gas is 80%. The conditions of reduction are 450° C., 0.3 MPa (absolute pressure) and 800 h$^{-1}$. The time of reduction is 4 h. The content of halogen in the catalyst after reduction is 53.62% of the total content of halogen in the catalyst before reduction. After the reaction has become stable for one hour, samples are taken and analyzed. The reaction result is shown in Table 1.

Example 12

Weigh an appropriate amount of zinc chloride, dissolve it in deionized water, support it to aluminum oxide (pore volume 0.71 ml/g, specific surface area 236 m²/g, bar type, equivalent diameter 1.5 mm) support by the method of incipient wetness impregnation, dry at 120° C. for 4 h and calcinate at 500° C. for 4 h to obtain catalyst precursor ZnO/Al$_2$O$_3$. Put 5 g of the catalyst precursor in a continuous flow fixed bed reactor and treat the catalyst precursor with a mixed gas of monobromomethane and nitrogen of which volume concentration of monobromomethane is 80% under the conditions of 250° C., 0.3 MPa (absolute pressure), 300 h$^{-1}$ and 2 h to obtain a catalyst for preparation of isobutylene from halomethane, marked as C-12. The weight composition of the obtained catalyst is that the weight content of ZnBr$_2$ as to bromide is 30%, the weight content of ZnO as to oxide is 4%, the total acidity of 450° C. or less in the catalyst is 0.87 mmol/g, and the acidity of 250° C.-350° C. is 65.7% of the total acidity of 450° C. or less.

The reaction for preparation of isobutylene from bromomethane takes place in a continuous fluidized fixed bed micro-reactor. The loading amount of catalyst is 5 g. The feed gas is a mixed gas of monobromomethane and nitrogen of which volume concentration of monobromomethane is 70%. The reaction temperature is 230° C., reaction pressure is 2 MPa (absolute pressure) and space velocity is 200 h$^{-1}$. Before input of feed gas, the catalyst is activated in a mixed atmosphere containing hydrogen. The volume content of hydrogen in the mixed gas is 80%. The conditions of reduction are 450° C., 0.3 MPa (absolute pressure) and 800 h$^{-1}$. The time of reduction is 4 h. The content of halogen in the catalyst after reduction is 47.89% of the total content of halogen in the catalyst before reduction. After the reaction has become stable for one hour, samples are taken and analyzed. The reaction result is shown in Table 1.

Example 13

Weigh an appropriate amount of zinc nitrate, dissolve it in deionized water, support it to silicon dioxide (pore volume 1.06 ml/g, specific surface area 387 m$^2$/g, spherical shape, equivalent diameter 0.5 mm) support by the method of incipient wetness impregnation, dry at 120° C. for 4 h and calcinate at 500° C. for 4 h to obtain catalyst precursor ZnO/SiO$_2$. Put 5 g of the catalyst precursor in a continuous flow fixed bed reactor and treat the catalyst precursor with a mixed gas of monobromomethane and nitrogen of which volume concentration of monobromomethane is 80% under the conditions of 250° C., 0.3 MPa (absolute pressure), 300 h$^{-1}$ and 2 h to obtain a catalyst for preparation of isobutylene from halomethane, marked as C-13. The weight composition of the obtained catalyst is that the weight content of ZnBr$_2$ as to bromide is 30%, the weight content of ZnO as to oxide is 4%, the total acidity of 450° C. or less in the catalyst is 1.08 mmol/g, and the acidity of 250° C.-350° C. is 49.7% of the total acidity of 450° C. or less.

The reaction for preparation of isobutylene from bromomethane takes place in a continuous fluidized fixed bed micro-reactor. The loading amount of catalyst is 5 g. The feed gas is a mixed gas of monobromomethane and nitrogen of which volume concentration of monobromomethane is 70%. The reaction temperature is 230° C., reaction pressure is 2 MPa (absolute pressure) and space velocity is 200 h$^{-1}$. Before input of feed gas, the catalyst is activated in a mixed atmosphere containing hydrogen. The volume content of hydrogen in the mixed gas is 80%. The conditions of reduction are 400° C., 0.3 MPa (absolute pressure) and 800 h$^{-1}$. The time of reduction is 4 h. The content of halogen in the catalyst after reduction is 31.28% of the total content of halogen in the catalyst before reduction. After the reaction has become stable for one hour, samples are taken and analyzed. The reaction result is shown in Table 1.

Example 14

Weigh an appropriate amount of zinc nitrate, dissolve it in deionized water, support it to hydrogen-type ZSM-5 (silica-alumina mole ratio 50, pore volume 0.23 ml/g, specific surface area 426 m$^2$/g, bar type, equivalent diameter 1.5 mm) support by the method of incipient wetness impregnation, dry at 120° C. for 4 h and calcinate at 500° C. for 4 h to obtain catalyst precursor ZnO/H-ZSM-5. Put 5 g of the catalyst precursor in a continuous flow fixed bed reactor and treat the catalyst precursor with mixed gas of monobromomethane and nitrogen of which volume concentration of monobromomethane is 80% under the conditions of 250° C., 0.3 MPa (absolute pressure), 300 h$^{-1}$ and 2 h to obtain a catalyst for preparation of isobutylene from halomethane, marked as C-14. The weight composition of the obtained catalyst is that the weight content of ZnBr$_2$ as to bromide is 30%, the weight content of ZnO as to oxide is 4%, the total acidity of 450° C. or less in the catalyst is 0.74 mmol/g, and the acidity of 250° C.-350° C. is 48.7% of the total acidity of 450° C. or less.

The reaction for preparation of isobutylene from bromomethane takes place in a continuous fluidized fixed bed micro-reactor. The loading amount of catalyst is 5 g. The feed gas is a mixed gas of monobromomethane and nitrogen of which volume concentration of monobromomethane is 70%. The reaction temperature is 230° C., reaction pressure is 2 MPa (absolute pressure) and space velocity is 200 h$^{-1}$. Before input of feed gas, the catalyst is activated in a mixed atmosphere containing hydrogen. The volume content of hydrogen in the mixed gas is 80%. The conditions of reduction are 400° C., 0.3 MPa (absolute pressure) and 800 h$^{-1}$. The time of reduction is 4 h. The content of halogen in the catalyst after reduction is 79.73% of the total content of halogen in the catalyst before reduction. After the reaction has become stable for one hour, samples are taken and analyzed. The reaction result is shown in Table 1.

Example 15

Weigh an appropriate amount of zinc nitrate, dissolve it in deionized water, support it to aluminum oxide (pore volume 0.71 ml/g, specific surface area 236 m$^2$/g, bar type, equivalent diameter 1.5 mm) support by the method of incipient wetness impregnation, dry at 120° C. for 4 h and calcinate at 500° C. for 4 h to obtain catalyst precursor ZnO/Al$_2$O$_3$. Put 5 g of the catalyst precursor in a continuous flow fixed bed reactor and treat the catalyst precursor with a mixed gas of monobromomethane and nitrogen of which volume concentration of monobromomethane is 80% under the conditions of 250° C., 0.3 MPa (absolute pressure), 300 h$^{-1}$ and 2 h. Weigh an appropriate amount of zirconium nitrate, dissolve it in deionized water, impregnate bromized sample by the method of incipient wetness impregnation, dry at 120° C. in a nitrogen atmosphere for 4 h and calcinate at 500° C. in a nitrogen atmosphere for 4 h to obtain a catalyst for preparation of isobutylene from halomethane, marked as C-15. The weight composition of the obtained catalyst is that the weight content of ZnBr$_2$ as to bromide is 30%, the weight content of ZnO as to oxide is 4%, the weight content of Zr as to element is 1%, the total acidity of 450° C. or less in the catalyst is 0.72 mmol/g, and the acidity of 250° C.-350° C. is 71.4% of the total acidity of 450° C. or less.

The reaction for preparation of isobutylene from bromomethane takes place in a continuous fluidized fixed bed micro-reactor. The loading amount of catalyst is 5 g. The feed gas is a mixed gas of monobromomethane and nitrogen of which volume concentration of monobromomethane is 70%. The reaction temperature is 230° C., reaction pressure is 2 MPa (absolute pressure) and space velocity is 200 h$^-$. Before input of feed gas, the catalyst is activated in a mixed atmosphere containing hydrogen. The volume content of hydrogen in the mixed gas is 80%. The conditions of reduction are 450° C., 0.3 MPa (absolute pressure) and 800 h$^{-1}$. The time of reduction is 4 h. The content of halogen in the catalyst after reduction is 42.57% of the total content of halogen in the catalyst before reduction. After the reaction has become stable for one hour, samples are taken and analyzed. The reaction result is shown in Table 1.

Example 16

Weigh an appropriate amount of zinc nitrate, dissolve it in deionized water, support it to aluminum oxide (pore volume 0.71 ml/g, specific surface area 236 m²/g, bar type, equivalent diameter 1.5 mm) support by the method of incipient wetness impregnation, dry at 120° C. for 4 h and calcinate at 500° C. for 4 h to obtain catalyst precursor ZnO/Al$_2$O$_3$. Put 5 g of the catalyst precursor in a continuous flow fixed bed reactor and treat the catalyst precursor with a mixed gas of monobromomethane and nitrogen of which volume concentration of monobromomethane is 80% under the conditions of 250° C., 0.3 MPa (absolute pressure), 300 h$^{-1}$ and 2 h. Weigh an appropriate amount of cerium nitrate, dissolve it in deionized water, impregnate bromized sample by the method of incipient wetness impregnation, dry at 80° C. in a nitrogen atmosphere for 8 h and calcainate at 500° C. in a nitrogen atmosphere for 4 h to obtain a catalyst for preparation of isobutylene from halomethane, marked as C-16. The weight composition of the obtained catalyst is that the weight content of ZnBr$_2$ as to bromide is 30%, the weight content of ZnO as to oxide is 4%, the weight content of Ce as to element is 0.5%, the total acidity of 450° C. or less in the catalyst is 0.81 mmol/g, and the acidity of 250° C.-350° C. is 69.3% of the total acidity of 450° C. or less.

The reaction for preparation of isobutylene from bromomethane takes place in a continuous fluidized fixed bed micro-reactor. The loading amount of catalyst is 5 g. The feed gas is a mixed gas of monobromomethane and nitrogen of which volume concentration of monobromomethane is 70%. The reaction temperature is 230° C., reaction pressure is 2 MPa (absolute pressure) and space velocity is 200 h$^{-1}$. Before input of feed gas, the catalyst is activated in a mixed atmosphere containing hydrogen. The volume content of hydrogen in the mixed gas is 80%. The conditions of reduction are 450° C., 0.3 MPa (absolute pressure) and 500 h$^{-1}$. The time of reduction is 6 h. The content of halogen in the catalyst after reduction is 65.49% of the total content of halogen in the catalyst before reduction. After the reaction has become stable for one hour, samples are taken and analyzed. The reaction result is shown in Table 1.

Example 17

A supported catalyst is prepared and the reaction for preparing isobutylene from bromomethane takes place according to the methods described in Example 16 except that aluminum oxide with pore volume of 0.51 ml/g, specific surface area of 162.4 m²/g, bar type and equivalent diameter of 1 mm is used as a support to obtain a catalyst for preparation of isobutylene from halomethane, marked as C-17. The total acidity of 450° C. or less in the obtained catalyst is 0.72 mmol/g, and the acidity of 250° C.-350° C. is 70.5% of the total acidity of 450° C. or less. The content of halogen in the catalyst after reduction activation is 72.57% of the total content of halogen in the catalyst before reduction. The catalyst properties and reaction result are shown in Table 1.

Example 18

A supported catalyst is prepared and the reaction for preparing isobutylene from bromomethane takes place according to the methods described in Example 16 except that bromomethane is substituted with dichloromethane in equal molar weight. The result indicates the conversion rate of dichloromethane is 97.4%, and the selectivity of isobutylene is 67.9%.

Comparative Example 1

Weigh an appropriate amount of zinc nitrate, dissolve it in deionized water, support it to aluminum oxide (pore volume 0.71 ml/g, specific surface area 236 m²/g, bar type, equivalent diameter 1.5 mm) support by the method of incipient wetness impregnation, dry at 120° C. for 4 h and calcinate at 500° C. for 8 h to obtain catalyst ZnO/Al$_2$O$_3$, marked as D-1. The weight composition of the obtained catalyst is that the weight content of ZnO as to oxide is 20%, the total acidity of 450° C. or less in the catalyst is 0.49 mmol/g, and the acidity of 250° C.-350° C. is 44.5% of the total acidity of 450° C. or less.

The reaction for preparation of isobutylene from bromomethane takes place in a continuous fluidized fixed bed micro-reactor. The loading amount of catalyst is 5 g. The feed gas is a mixed gas of monobromomethane and nitrogen of which volume concentration of monobromomethane is 30%. The reaction temperature is 270° C., reaction pressure is 2 MPa (absolute pressure) and space velocity is 350 h$^{-1}$. Before input of feed gas, the catalyst is activated in a hydrogen atmosphere. The volume content of hydrogen in the mixed gas is 70%. The conditions of reduction are 350° C., 0.3 MPa (absolute pressure) and 800 h$^{-1}$. The time of reduction is 6 h. After the reaction has become stable for one hour, samples are taken and analyzed. The reaction result is shown in Table 1.

Comparative Example 2

Weigh an appropriate amount of zinc nitrate, dissolve it in deionized water, support it to aluminum oxide (pore volume 0.71 ml/g, specific surface area 236 m²/g, bar type, equivalent diameter 1.5 mm) support by the method of incipient wetness impregnation, dry at 120° C. for 4 h and calcinate at 500° C. for 8 h to obtain catalyst precursor ZnO/Al$_2$O$_3$. Put 5 g of the catalyst precursor in a continuous flow fixed bed reactor and treat the catalyst precursor with a mixed gas of monobromomethane and nitrogen of which volume concentration of monobromomethane is 80% under the conditions of 250° C., 0.3 MPa (absolute pressure), 300 h$^{-1}$ and 2 h to obtain a catalyst for preparation of isobutylene from halomethane, marked as D-2. The weight composition of the obtained catalyst is that the weight content of ZnBr$_2$ as to bromide is 30%, the weight content of ZnO as to oxide is 4%, the total acidity of 450° C. or less in the catalyst is 0.93 mmol/g, and the acidity of 250° C.-350° C. is 63.2% of the total acidity of 450° C. or less.

The reaction for preparation of isobutylene from bromomethane takes place in a continuous fluidized fixed bed micro-reactor. The loading amount of catalyst is 5 g. The feed gas is a mixed gas of monobromomethane and nitrogen of which volume concentration of monobromomethane is 70%. The reaction temperature is 230° C., reaction pressure is 2 MPa (absolute pressure) and space velocity is 200 h$^{-1}$. After the reaction has become stable for one hour, samples are taken and analyzed. The reaction result is shown in Table 1.

Comparative Example 3

Weigh an appropriate amount of zinc bromide, dissolve it in deionized water, support it to aluminum oxide (pore volume 0.71 ml/g, specific surface area 236 m²/g, bar type, equivalent diameter 1.5 mm) support by the method of incipient wetness impregnation, dry at 80° C. in a nitrogen atmosphere for 4 h and calcinate at 500° C. in a nitrogen atmosphere for 4 h to obtain catalyst ZnBr$_2$/Al$_2$O$_3$, marked as D-3. The weight composition of the obtained catalyst is that the weight content of ZnBr$_2$ as to bromide is 30%, the total acidity of 450° C. or less in the catalyst is 1.01 mmol/g, and the acidity of 250° C.-350° C. is 74.3% of the total acidity of 450° C. or less.

The reaction for preparation of isobutylene from bromomethane takes place in a continuous fluidized fixed bed micro-reactor. The loading amount of catalyst is 5 g. The feed gas is a mixed gas of monobromomethane and nitrogen of which volume concentration of monobromomethane is 70%. The reaction temperature is 230° C., reaction pressure is 2 MPa (absolute pressure) and space velocity is 200 $h^{-1}$. Before input of feed gas, the catalyst is activated in a mixed atmosphere containing hydrogen. The volume content of hydrogen in the mixed gas is 80%. The conditions of reduction are 450° C., 0.3 MPa (absolute pressure) and 800 $h^{-1}$. The time of reduction is 4 h. The content of halogen in the catalyst after reduction is 91.27% of the total content of halogen in the catalyst before reduction. After the reaction has become stable for one hour, samples are taken and analyzed. The reaction result is shown in Table 1.

TABLE 1

Catalyst reactivity

| Catalyst | zinc oxide wt. % | zinc halide wt. % | promoter wt. % | Support | Total acidity mmol/g | Acid ratio % | Bromomethane conversion rate, % | Isobutylene selectivity, % |
|---|---|---|---|---|---|---|---|---|
| C-1 | 6 | 27 (ZnBr$_2$) | 0 | Al$_2$O$_3$ | 0.92 | 55.1 | 94.5 | 73.4 |
| C-2 | 4 | 30 (ZnBr$_2$) | 0 | Al$_2$O$_3$ | 0.93 | 63.2 | 99.4 | 82.5 |
| C-3 | 2 | 33 (ZnBr$_2$) | 0 | Al$_2$O$_3$ | 0.95 | 75.5 | 92.1 | 81.6 |
| C-4 | 2 | 18 (ZnBr$_2$) | 0 | Al$_2$O$_3$ | 0.72 | 66.8 | 96.2 | 86.3 |
| C-5 | 6 | 39 (ZnBr$_2$) | 0 | Al$_2$O$_3$ | 0.98 | 64.1 | 97.8 | 91.2 |
| C-6 | 9 | 35 (ZnBr$_2$) | 0 | Al$_2$O$_3$ | 0.94 | 57.3 | 91.5 | 78.7 |
| C-7 | 1 | 20 (ZnBr$_2$) | 0 | Al$_2$O$_3$ | 0.79 | 74.9 | 91.4 | 82.7 |
| C-8 | 4 | 30 (ZnBr$_2$) | 2(Zr) | Al$_2$O$_3$ | 0.97 | 69.7 | 99.3 | 84.2 |
| C-9 | 4 | 30 (ZnBr$_2$) | 1(Ce) | Al$_2$O$_3$ | 0.91 | 68.9 | 98.5 | 88.2 |
| C-10 | 4 | 30 (ZnBr$_2$) | 0.5(La) | Al$_2$O$_3$ | 0.87 | 65.3 | 97.8 | 86.6 |
| C-11 | 4 | 30 (ZnBr$_2$) | 3(Ti) | Al$_2$O$_3$ | 0.96 | 63.4 | 95.9 | 88.5 |
| C-12 | 4 | 30 (ZnBr$_2$) | 0 | Al$_2$O$_3$ | 0.87 | 65.7 | 95.4 | 84.3 |
| C-13 | 4 | 30 (ZnBr$_2$) | 0 | SiO$_2$ | 1.08 | 49.7 | 57.8 | 71.1 |
| C-14 | 4 | 30 (ZnBr$_2$) | 0 | ZSM-5 | 0.74 | 48.7 | 92.6 | 52.2 |
| C-15 | 4 | 30 (ZnBr$_2$) | 1(Zr) | Al$_2$O$_3$ | 0.72 | 71.4 | 94.2 | 91.3 |
| C-16 | 4 | 30 (ZnBr$_2$) | 0.5(Ce) | Al$_2$O$_3$ | 0.81 | 69.3 | 92.5 | 86.7 |
| C-17 | 4 | 30 (ZnBr$_2$) | 0.5(Ce) | Al$_2$O$_3$ | 0.72 | 70.5 | 93.6 | 76.4 |
| D-1 | 20 | 0 | 0 | Al$_2$O$_3$ | 0.49 | 44.5 | 99.7 | 0 |
| D-2 | 4 | 30 (ZnBr$_2$) | 0 | Al$_2$O$_3$ | 0.93 | 63.2 | 0 | 0 |
| D-3 | 0 | 30 (ZnBr$_2$) | 0 | Al$_2$O$_3$ | 1.01 | 74.3 | 8.31 | 0 |

The result is in Table 1 indicate the catalyst of the present invention has obviously higher bromomethane conversion rate and isobutene selectivity.

What is claimed is:

1. A supported catalyst, comprising:
   a support and an active component supported on the support,
   wherein the active component contains zinc oxide and zinc halide, and a content of zinc oxide is 0.5 wt. %-20 wt. %, a content of zinc halide is 10 wt. %-50 wt. %, and a content of the support is 40 wt. %-88 wt. %, based on a total weight of the catalyst,
   wherein the supported catalyst catalyzes a conversion of halomethane to isobutylene.

2. The supported catalyst according to claim 1, wherein the content of zinc oxide is 1 wt. %-15 wt. %, the content of zinc halide is 15 wt. %-40 wt. %, and the content of the support is 50 wt. %-84 wt. % based on the total weight of the catalyst.

3. The supported catalyst according to claim 2, wherein the content of zinc oxide is 1 wt. %-9 wt. %, the content of zinc halide is 18 wt. %-39 wt. %, and the content of the support is 55 wt. %-80 wt. % based on the total weight of the catalyst.

4. The supported catalyst according to claim 1, wherein the zinc halide is selected from the group consisting of zinc fluoride, zinc chloride, zinc bromide, zinc iodide, and mixtures thereof, and the support is selected from the group consisting of aluminum oxide, silicon oxide, ZSM-5 molecular sieve, and mixtures thereof.

5. The supported catalyst according to claim 4, wherein the zinc halide is zinc bromide, and the support is aluminum oxide.

6. The supported catalyst according to claim 1, further comprising a promoter selected from the group consisting of Ti, Zr, Ce, La, and mixtures thereof, and a content of the promoter calculated on element is 0.1 wt. %-10 wt. % based on the total weight of the catalyst.

7. The supported catalyst according to claim 6, wherein the promoter is Zr, and the weight content of the promoter calculated on element is 0.5 wt. %-5 wt. % based on the total weight of the catalyst.

8. The supported catalyst according to claim 1, wherein having a total acidity at a NH$_3$ desorption temperature of 450° C. or less of 0.5 mmol/g-1.3 mmol/g, and the acidity at the NH$_3$ desorption temperature of 250° C.-350° C. is 20%-90% of the total acidity at the NH$_3$ desorption temperature of 450° C. or less, measured using a NH$_3$-Temperature Programed Desorption (NH$_3$-TPD) method.

9. A method for preparing the supported catalyst of claim 1, comprising:
   introducing zinc oxide to a support thereby producing a supported zinc oxide; and
   halogenating the supported zinc oxide.

10. The method according to claim 9, wherein the halogenation step comprises contacting a halogen-containing compound with the supported zinc oxide to partially convert zinc oxide into zinc halide.

11. The method according to claim 10, wherein a content of the support is 40%-88% based on a total weight of the supported catalyst, and a content of zinc oxide on the support is 0.5%-20%, and a content of zinc halide is 10%-50%.

12. The method according to claim 10, wherein the halogen-containing compound is in a mixture containing the halogen-containing compound and an inert gas, and a concentration of the halogen-containing compound in the mixture is not less than 20 v/v %.

13. The method according to claim 12, wherein the halogen-containing compound is one or more chosen from monohalomethane, bihalomethane, or trihalomethane.

14. The method according to claim 12, wherein the contact step comprises putting the supported zinc oxide in a continuous flow fixed bed reactor, raising temperature to 150° C.-400° C. in an inert atmosphere, and feeding the halogen-containing compound at a space velocity of 50 $h^{-1}$-1000 $h^{-1}$ under a pressure of 0.1 MPa-0.5 MPa for 0.5 h-8 h.

15. A method for preparation of isobutylene from halomethane, comprising:
activating the supported catalyst according to claim 1 by reduction in hydrogen so that a content of halogen in the activated catalyst is 20 wt. %-90 wt. % of a total content of halogen in the supported catalyst before activation, then contacting halomethane with the activated catalyst to prepare isobutylene.

16. The method according to claim 15, wherein the contact step is carried out at a reaction temperature of 150° C.-350° C. under a reaction pressure of 0.1 MPa-5 MPa and a space velocity 50 $h^{-1}$-1000 $h^{-1}$.

17. The method according to claim 15, wherein the content of halogen in the activated catalyst is 30 wt %-80 wt % of the total content of halogen in the supported catalyst.

18. The method according to claim 15, wherein the activation step comprises raising a temperature of the supported catalyst to 300° C.-600° C. in an inert atmosphere; and exposing the supported catalyst to hydrogen or a mixed gas of hydrogen and inert gas containing 10 vol %-95 vol % of hydrogen, at a space velocity of 200 $h^{-1}$-2000 $h^{-1}$ under a pressure of 0.1 MPa-0.5 MPa for 2 h-16 h.

19. The method according to claim 15, wherein halomethane is one or more of monohalomethane, bihalomethane, or trihalomethane.

20. The method according to claim 15, wherein the contacting step is carried out in a fixed bed, a fluidized bed, a fixed fluidized bed, a moving bed, a slurry bed, or a bubbling bed reactor.

* * * * *